United States Patent
Marggi

(10) Patent No.: US 6,302,866 B1
(45) Date of Patent: Oct. 16, 2001

(54) CATHETER HEAD FOR SUBCUTANEOUS ADMINISTRATION OF AN SUBSTANCE

(75) Inventor: Rolf Marggi, Bern (CH)

(73) Assignee: Disetronic Licensing AG (CH)

(*) Notice: Subject to any disclaimer, the term of this patent is extended or adjusted under 35 U.S.C. 154(b) by 0 days.

(21) Appl. No.: 09/311,022

(22) Filed: May 13, 1999

(30) Foreign Application Priority Data

May 14, 1998 (DE) .............................. 198 21 723

(51) Int. Cl.[7] .................................................. A61M 5/00
(52) U.S. Cl. .................................... 604/174; 604/506
(58) Field of Search .................................. 604/174, 151, 604/177, 171, 131, 164.08, 164.02, 506, 507, 508, 511

(56) References Cited

U.S. PATENT DOCUMENTS

| | | | |
|---|---|---|---|
| 3,783,868 | 1/1974 | Bokros | 128/260 |
| 4,436,519 | 3/1984 | O'Neill | 604/175 |
| 4,475,548 | 10/1984 | Muto | 128/207.14 |
| 4,537,593 | 8/1985 | Alchas | 604/411 |
| 4,682,981 | 7/1987 | Suzuki et al. | 604/158 |
| 4,880,412 * | 11/1989 | Weiss | 604/165 |
| 4,886,501 | 12/1989 | Johnston et al. | 604/175 |
| 4,966,588 | 10/1990 | Rayman et al. | 604/165 |
| 5,033,476 | 7/1991 | Kasai | 128/764 |
| 5,084,060 | 1/1992 | Freund et al. | 606/192 |
| 5,092,849 | 3/1992 | Sampson | 604/175 |
| 5,104,389 | 4/1992 | Deem et al. | 604/264 |
| 5,171,231 | 12/1992 | Heiliger | 604/263 |
| 5,209,739 | 5/1993 | Talalay | 604/195 |
| 5,281,199 | 1/1994 | Ensimnger et al. | 604/93 |
| 5,286,453 | 2/1994 | Pope | 422/100 |
| 5,337,756 | 8/1994 | Barbier et al. | 128/763 |
| 5,429,609 | 7/1995 | Yoon | 604/167 |
| 5,460,616 | 10/1995 | Weinstein et al. | 604/167 |
| 5,466,230 | 11/1995 | Davila | 604/256 |
| 5,474,534 * | 12/1995 | Schlitt | 604/177 X |
| 5,522,803 | 6/1996 | Teissen-Simony | 604/177 |
| 5,573,510 | 11/1996 | Isaacson | 604/158 |
| 5,776,125 | 7/1998 | Dudar et al. | 606/411 |
| 5,782,817 | 7/1998 | Franzel et al. | 604/256 |
| 5,814,026 | 9/1998 | Yoon | 604/280 |
| 5,827,244 | 10/1998 | Boettger | 604/283 |
| 6,010,494 | 1/2000 | Schäfer et al. | 604/533 |
| 6,071,265 | 6/2000 | Bestetti et al. | 604/256 |

FOREIGN PATENT DOCUMENTS

| | | |
|---|---|---|
| 5861273 | 1/1975 | (AU) . |
| 0143895 | 4/1986 | (EP) . |
| WO 9415660 | 7/1994 | (WO) . |

* cited by examiner

Primary Examiner—John D. Yasko
(74) Attorney, Agent, or Firm—Dorsey & Whitney LLP

(57) ABSTRACT

The present invention provides a catheter head including a cannula housing, a needle holder connectable to the cannula housing and a guide sleeve associated with the needle holder for positioning and guiding a connecting needle, and for being narrowly slide-guided over a portion of said cannula housing.

11 Claims, 5 Drawing Sheets

CATHETER HEAD FOR SUBCUTANEOUS ADMINISTRATION OF AN SUBSTANCE

RELATED APPLICATIONS

This application claims the priority of German Patent Application No. 198 21 723.4, filed May 14, 1998, which is incorporated herein by reference.

BACKGROUND

The invention relates to a catheter head for subcutaneous administration of substances, including medically active substances, such as insulin and the like.

A catheter head as known from U.S. Pat. No. 5,522,803 comprises a cannula housing with a cannula and a needle holder, to be connected to the cannula housing, including a feed line for feeding a substance to the catheter head. The cannula projects from the cannula housing and is placed in tissue. In the cannula housing a passage channel to the cannula is formed for the active substance. The cannula housing is designed to allow flush, conforming or mould (or molded) positioning on the surface of the tissue into which the cannula is placed, and it is prepared for being fixed on or attached to the tissue.

A connecting needle is rigidly attached to the needle holder. The connecting needle is introduced into the passage channel of the cannula housing for obtaining a connection. Both the cannula and the cannula housing will stay on the site of attachment in and on the tissue, whereas the needle holder may be repeatedly connected to the cannula housing and separated from the same again. During assembly, the cannula housing and the needle holder are automatically engaging into each other, due to the needle holder detachably anchoring itself to the cannula housing. Guide means are provided for positioning the connecting needle in relation to the passage channel of the cannula housing and for introducing the connecting needle into the passage channel, with the guide means guiding the needle holder at the cannula housing.

The guide means of this known catheter head are formed by a pair of guide pins projecting on either side of the connecting needle and parallel to the same from the needle holder. Accordingly, the cannula housing is provided with guide shafts on either side of an inlet into the passage channel into which one each of the guide pins for introducing the connecting needle is inserted. The connecting needle is positioned in relation to the inlet by the interaction of the guide pins with the guide shafts and guided in centered position during introduction into the passage channel. In the course of advancement of the connecting needle in the passage channel, the needle holder is anchored by an automatically engaging snap-on connection to the cannula housing.

SUMMARY

It is an object of the invention to provide a catheter head for subcutaneous administration of a substance comprising a cannula housing and needle holder which may be simply and correctly connected to each other, and which is easy to manufacture.

In one embodiment, the present invention provides a catheter head comprising a cannula housing, a needle holder connectable to the cannula housing and a guide sleeve associated with the needle holder for positioning and guiding a connecting needle, and for being narrowly slide-guided over a portion of said cannula housing.

In one embodiment the catheter head to which the invention relates comprises a cannula housing with a cannula and a needle holder, to be connected to the cannula housing, including a feed line for feeding an active substance to the catheter head. The cannula projects from the cannula housing and is placed in tissue. The cannula may be an integral part of the cannula housing. In another embodiment, the cannula may be attached and/or anchored inside the cannula housing. It may be designed as a rigid element, such as a steel cannula, or it may be flexible, or pliable. In the cannula housing a passage channel to the cannula is formed for the active substance. The cannula housing is designed to allow flush positioning on the tissue, into which the cannula is placed, and it is prepared for being fixed on to the tissue.

A connecting needle is rigidly attached to the needle holder. The connecting needle is introduced into the passage channel of the cannula housing for obtaining a connection. Both the cannula and the cannula housing will stay on the site of attachment in and on the tissue, whereas the needle holder may be repeatedly connected to the cannula housing and separated from the same again. During connection or assembly, the cannula housing and the needle holder are preferably automatically engaging with each other, in particular due to the needle holder being detachably anchored to the cannula housing. Guide means are provided for positioning the connecting needle in relation to the passage channel of the cannula housing and for introducing the connecting needle into the passage channel, with the guide means guiding the needle holder at the cannula housing.

According to the invention, the guide means of the needle holder is a guide sleeve axially surrounding the connecting needle, said guide sleeve being pushed narrowly slide-guided over a cylindrical extension of the cannula housing upon the needle holder and the cannula housing being connected, i.e. upon the connecting needle being introduced. The cylindrical extension surrounds the inlet and a section of the passage channel of the cannula housing connected to the same. The invention ensures secure introduction of the connecting needle without the need of forming additional guide pins. In addition, the guide sleeve represents a means of protection for handling, both for the needle and the user. The guide sleeve may have openings, but is preferably designed as a closed sleeve body.

In one preferred embodiment, the cannula housing comprises a compact front section, from the underside of which the cannula projects and from the rear of which a disc-shaped section and the cylindrical extension project, the disc-shaped section extending the underside of the cannula housing placed on the tissue. An upper side of the disc-shaped rear section of the cannula housing facing the cylindrical extension and an underside of the needle holder are acting as additional guide means upon the cannula housing and the needle holder are being connected, preventing rotation of the needle holder in relation to the cannula housing around the longitudinal axis of the connecting needle.

Preferably, an additional passage is formed in the cannula housing for a piercing needle for the cannula. When the cannula housing and the needle holder are connected, this passage points at an angle in relation to the connecting needle. The passage channel for the connecting needle leads into this additional passage which extends the passage channel up to the cannula after the cannula has been placed and the piercing needle retracted. Owing to the fact that a piercing needle need not be retracted from the passage channel, into which the connecting needle is introduced after placing the cannula and fixing the cannula housing, complete precharging of the catheter head up to the cannula, i.e. priming, is possible in the state of the cannula housing and the needle holder being connected.

In another embodiment, a flexible cannula extends the passage channel, but flush. In a third embodiment, the cannula may be formed by the piercing needle itself.

In one manufacturing process, the prefabricated cannula is moulded into the cannula housing when injection-moulding the cannula housing. For this purpose, a rear section of the cannula is preferably provided with a widened section, anchoring the cannula in the cannula housing during injection. The cannula may be made of a soft plastic material, in particular Teflon. A thermoplastic material may be used both as a material for the cannula housing and for the needle holder.

Other objects, features, embodiments and advantages of the device and method of the present invention will become more fully apparent and understood with reference to the following description and appended drawings and claims.

DETAILED DESCRIPTION

The accompanying Figures and this description depict and describe embodiments of the catheter head and methods of the present invention, and features and components thereof. With regard to means for fastening, mounting, attaching or connecting the components of the present invention to form the device as a whole, unless specifically described otherwise, such means are intended to encompass conventional fasteners such as threaded connectors, snap rings, clamps such as screw clamps and the like, rivets, toggles, pins and the like. Components may also be connected by adhesives, glues, welding, ultrasonic welding, and friction fitting or deformation, if appropriate. Unless specifically otherwise disclosed or taught, materials for making components of the present invention may be selected from appropriate materials such as metal, metallic alloys, natural and manmade fibers, vinyls, plastics and the like, and appropriate manufacturing or production methods including casting, extruding, molding and machining may be used.

Any references to front and back, right and left, top and bottom and upper and lower are intended for convenience of description, not to limit the present invention or its components to any one positional or spacial orientation.

Figure 1:
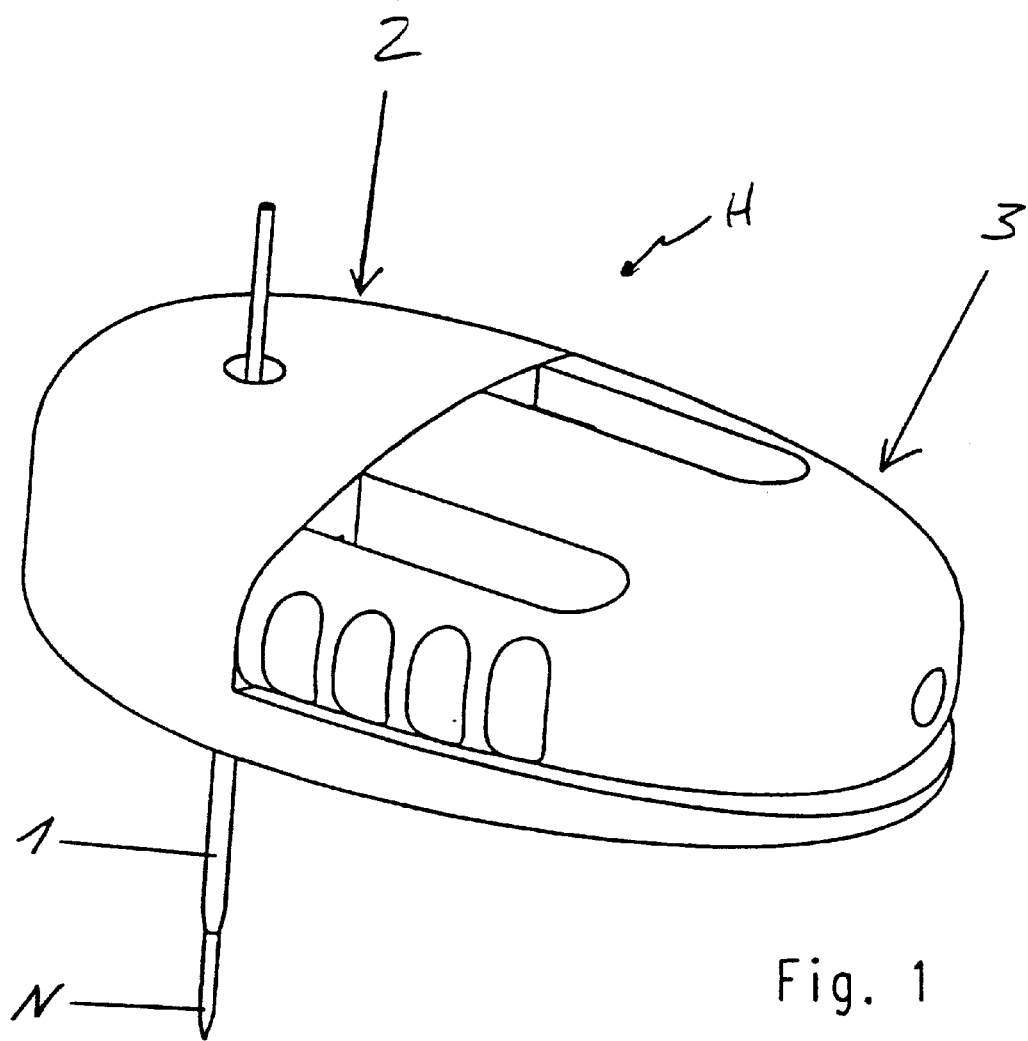
FIG. 1 depicts the catheter head in accordance with the present invention in assembled condition.

FIG. 1 shows a catheter head H comprising a cannula 1, extending vertically from an underside of the catheter head. The cannula 1, made of a soft plastic material, for example, Teflon, closely surrounds a piercing needle N, projecting through the catheter head H transversely, preferably vertically or perpendicularly, in relation to its generally flat, level underside. The catheter head H of FIG. 1 forms the front end of a catheter 5, as marked in FIGS. 2 to 4. The catheter with the catheter head H is set by the user himself, for instance a diabetic. For this purpose, the piercing needle N and the cannula 1 are inserted vertically under the skin into the tissue, and the underside of the catheter head is positioned adjacent to and/or fixed or attached to the skin. Fixation is effected by means of a self-adhesive pad or plaster. In one embodiment, the pad may enlarge the underside surface of the catheter head H available for adhesion. Should the underside as such provide an adhesive area of a sufficient size, provision of such an underside will be sufficient as an adhesive area After placing the cannula 1, the piercing needle N is retracted from the catheter head, with only the thin, flexible, pliable, cannula 1 remaining in the tissue.

The catheter head H further comprises a cannula housing 2, which remains at the point of piercing of the skin together with the cannula 1, with an underside for fixing the catheter head to the skin, and a needle holder 3, forming one front end of the catheter 5. The cannula housing 2 and the needle holder 3 are combined in a plug-in connection that may be repeatedly connected and disconnected.

Figure 2:
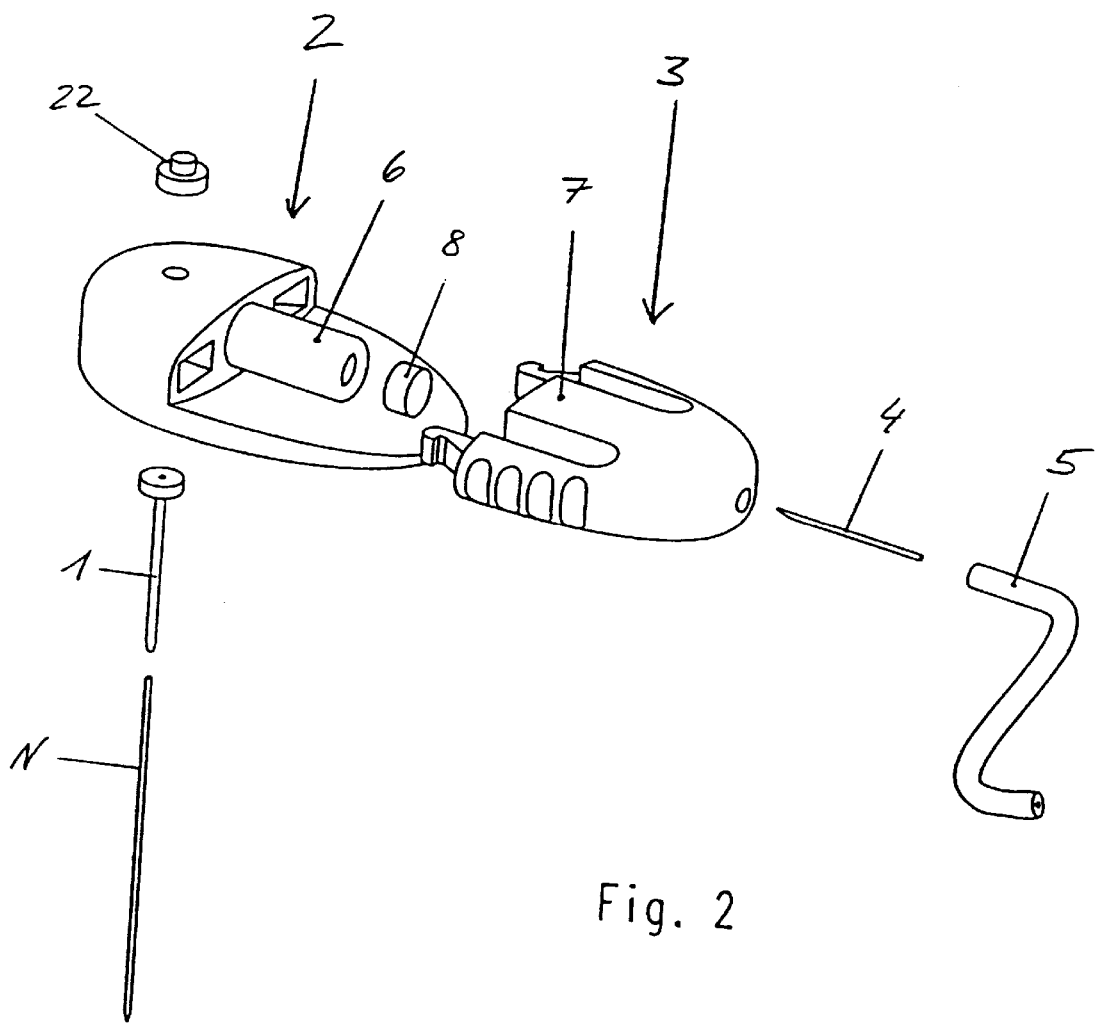
FIG. 2 is an exploded view of the catheter head depicted in FIG. 1, with components of the catheter head being shown individually and removed from their assembled position.

In FIG. 2, the cannula housing 2 and the needle holder 3 are shown detached or separated from each other, but aligned in relation to each other for being coupled or plugged together. Furthermore, the components of the catheter head H to be manufactured separately have been shown separated from their installed positions. All individual components have been aligned in relation to each other in accordance with their installation positions.

In use, an active substance is fed to the needle holder 3 through the catheter 5. It is passed through a connecting needle 4 within the needle holder 3 into a passage channel in the cannula housing 2, then to the cannula 1 and through the cannula 1 to the specified site into the issue. The piercing needle N shown in FIGS. 1 to 4 has been previously removed. An inlet 9 and an adjacent section of the passage channel of the cannula housing 2 are surrounded by a cylindrical extension 6, projecting from a rear side of the cannula housing 2. The passage within the catheter head H can be best seen in detail from the longitudinal section of FIG. 4.

Figure 3:
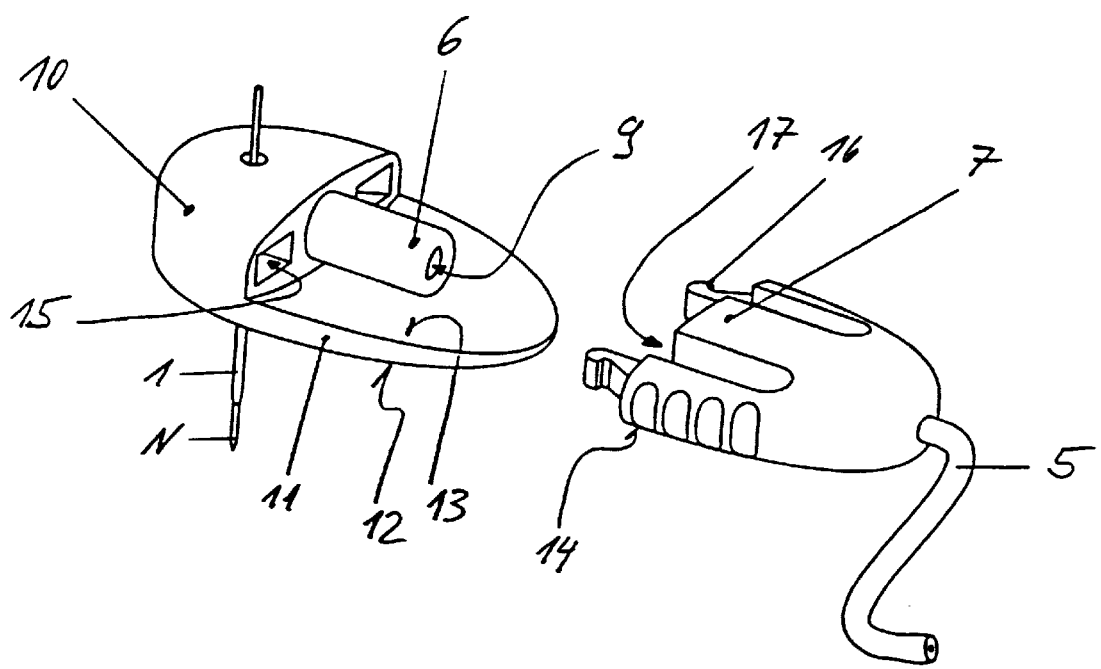
FIG. 3 depicts the catheter head according to FIG. 2 prior to assembly.

FIG. 3 shows the cannula housing 2 and the needle holder 3 with the individual components at their sites, each also arranged for assembly in a suitable position in relation to each other. From this position, the needle holder 3 is advanced in a straight line in longitudinal direction of the connecting needle 4, pointing towards the inlet 9, towards the cannula housing 2 and attached. The feed and attaching direction of the needle holder 3 extends generally parallel to the skin surface. The catheter is therefore leading away parallel to the skin surface, however, in some embodiments it may point away in an angle to the skin surface.

In assembled condition, the overall shape of the catheter head H is a semi-ovaloid, comprising a generally level underside 12. While the underside 12 is generally level or planar, in some embodiments it may be curved towards its edge, descending from the skin and ending in an upper side above, being in part convex and in part concave. The cannula housing 2, on which the underside 12 placed on the skin is formed, comprises a rear disc-shaped section 11 and a front section 10 thickened in relation to the same, from the underside 12 of which the cannula 1 and from the rear of which the cylindrical extension 6 and, facing the same, the disc-shaped section 11 project towards the rear into the direction of the needle holder 3, to be advanced towards the same. The upper side 13 of the rear section 11 is concave and rounded in shape, adapted to cooperate or compliment the curved underside 14 of the needle holder 3, being curved accordingly outwards. In contrast, the upper side of the front section 10 is curved convexly outwards. The needle holder 3 is of a symmetrical shape, i.e., its upper side and underside 14 are identically curved outwards. In addition, the needle holder 3 is symmetrical in plan view in relation to its central axis. The underside and the upper side of the needle holder 3 may be exchanged due to their symmetry when being plugged together with the cannula housing. This simplifies handling, due to correct alignment being verifiable easily by touch alone.

During interaction with a guide sleeve 7 provided on the needle holder 3, the cylindrical extension 6 acts as a guide means for positioning the connecting needle 4 in relation to the inlet 9 and for correct straight guidance of the connecting needle 4 within the section of the passage channel following the inlet 9. Thus, according to the invention, a part of the cannula housing 2 surrounding the passage channel, namely the cylindrical extension 6, is formed to project from the cannula housing 2 and allows to be used as a guide means for inserting the connecting needle 4. The guide means on the needle holder 3, interacting with the same, is formed by the guide sleeve 7, simultaneously protecting the connecting needle 4, coaxially arranged in the same, against damage. In addition, it protects the user against possible injury due to a projecting needle, for instance, when verifying alignment by touch due to a lack of attention during handling. The guide sleeve 7 projects over the connecting needle 4 in its longitudinal direction.

The guide sleeve 7 is formed by forming two longitudinal slots 17, i.e., the sleeve 7 is between these two slots 17 as a sleeve-shaped extension. In principle, the guide sleeve 7 could be formed by the needle holder 3 as a whole, i.e., being formed as a straight cylindrical recess in an otherwise full needle holder 3, which would then be regarded in total as a guide sleeve.

However, two elastic snap-on fingers 16 are formed by the slots 17 on either side of the guide sleeve 7, projecting over the guide sleeve 7. When attaching the needle holder 3, the snap-on fingers 16 engage with appropriate guide shafts 15, provided on either side of the cylindrical extension 6 in the cannula housing 2. During the insertion or joining of the connecting needle 4, the snap-on fingers 16 slide over guide faces of their guide shafts 15 tapered towards each other and are bent by the same towards each other. The elastically bendable snap-on fingers 16 are snapped out by their engaging tabs behind projections formed in the guide shafts 15 upon the connecting needle 4 having been completely inserted, thus anchoring the needle holder 3 at the cannula housing 2 by gripping behind the appropriate projections of the guide shafts. The snap-on connection is released by pressing the snap-on fingers 16 towards each other in their knurled sections. After having released the grip from behind in this way, the needle holder 3 may be retracted from the cannula housing 2.

Figure 4:
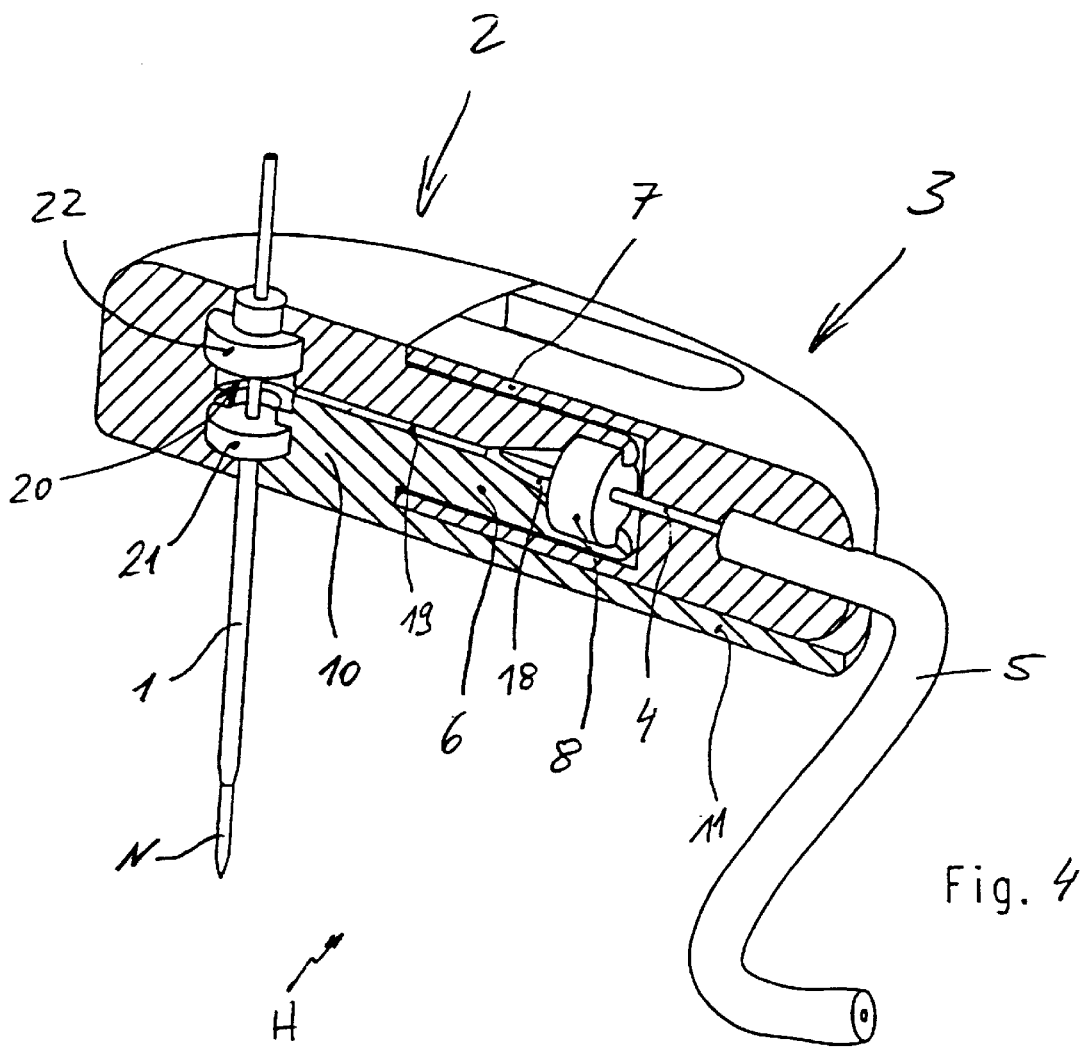
FIG. 4 is a longitudinal section depicting the catheter head according to FIGS. 1 to 3 in assembled condition.

FIG. 4 is a longitudinal section of the catheter head. The guide sleeve 7 is completely pushed over the cylindrical extension 6, with its front edge contacting the rear of the cannula housing 2, from which the cylindrical extension 6 projects. In this condition, the snap-on fingers 16 grip behind the appropriate tabs in the guide shafts 15. Therefore accidental release of the needle holder 3 is not possible.

When attaching the needle holder 3, the underside 14 of the needle holder 3 slides along the curved upper side 13 of the cannula housing 2. The guide sleeve 7 is positioned flush with the cylindrical extension 6 for positioning the connecting needle 4, wherein the needle holder 3 is displacable while being supported on the upper side 13 of the cannula housing 2. The cylindrical extension 6 is centered in the guide sleeve 7 when first being pushed over the cylindrical extension 6, due to the front edge of the cylindrical extension 6 being slightly rounded. Thereafter, the needle holder 3 is pushed forward over the cylindrical extension 6 with its guide sleeve 7, whereby the connecting needle 4 pierces a septum 8 directly arranged behind the inlet 9 in the passage channel of the cylindrical extension 6. The septum 8 is designed to hermetically seal the passage channel of the cannula housing 2 even after repeatedly being pierced. Directly behind the septum 8, the passage channel is provided with a domed section 18 into which the connecting needle 4 projects. A straight channel section 19, leading into a cavity 20 in the front section 10 of the cannula housing 2, arranged flush with the connecting needle 4, follows the domed section 18. The cannula 1, too, ends in the said cavity 20. The piercing needle N projects through the cavity forming, in this embodiment, a right angle to the connecting needle 4 and the channel section 19. The piercing needle N projects through the cannula housing 2, extending in an angle, in this embodiment, in a right angle to its underside 12. In this arrangement, the piercing needle N is advantageoulsy not guided through that part of the passage channel of the cannula housing 2 into which the connecting needle 4 is introduced. In this arrangement, the piercing needle N need not be removed in order to be able to introduce the connecting needle into the cannula housing. This is advantageous for so-called "priming," during which the catheter head H is being filled as far as possible completely with the active substance prior to placing the cannula 1. This considerably simplifies handling.

The cannula 1 is designed as a thin tube, comprising a flange-type widened section 21 at one end. The flange-type widened section 21 is placed in a disc-shaped recess of the cannula housing 2, thus anchoring the cannula 1.

Another septum 22 is inserted opposite the cannula inlet in the cavity 20, sealing the cavity 20, which forms part of the passage channel of the cannula housing 2, after retracting the piercing needle N. The function of the septum 22 is comparable with that of the septum 8. The shape of the cavity 20 is mainly cylindrical, with the flange-type widened section 21 of the cannula 1 and the septum 22 forming the opposite faces of the cylindrical cavity 20, between which the channel section 19 ends. For priming, the piercing needle N comprises an opening in its section located between the flange-type widened section 21 and the septum 22.

FIG. 4 clearly shows the flush support of the needle holder 3 over the full surface of the upper side 13 of the disc-shaped rear section 11 of the cannula housing 2. In addition, it is shown that a clearance remains between the upper side 13 and the cylindrical extension 6 into which the guide sleeve 7 enters upon the needle holder 3 being plugged-on. In principle, the said clearance between the disc-shaped section 11 and the cylindrical extension 6 is not required. The cylindrical extension 6 could, for instance, be located flat directly on the disc-shaped section 11. In this design, the underside of the guide sleeve 7 would be suitably open. The internal jacket face, being the actual slideway (or race-like guiding and supporting structure or travel path) for the guide sleeve 7 and the external jacket face of the cylindrical extension 6, need not be straight and circular or cylindrical in shape, although this is preferred, as long as sufficient slideway faces are available for positioning and neatly guiding the connecting needle 4. Guidance and security of the needle holder 3 against rotation in relation to the fixed cannula housing 2 is improved by the upper side 13 of the cannula housing 2 and the underside 14 of the needle holder 3 acting as slideways. The shape of these two guide faces 13 and 14 ensures correct alignment, in particular centering, during assembly.

Figure 5:
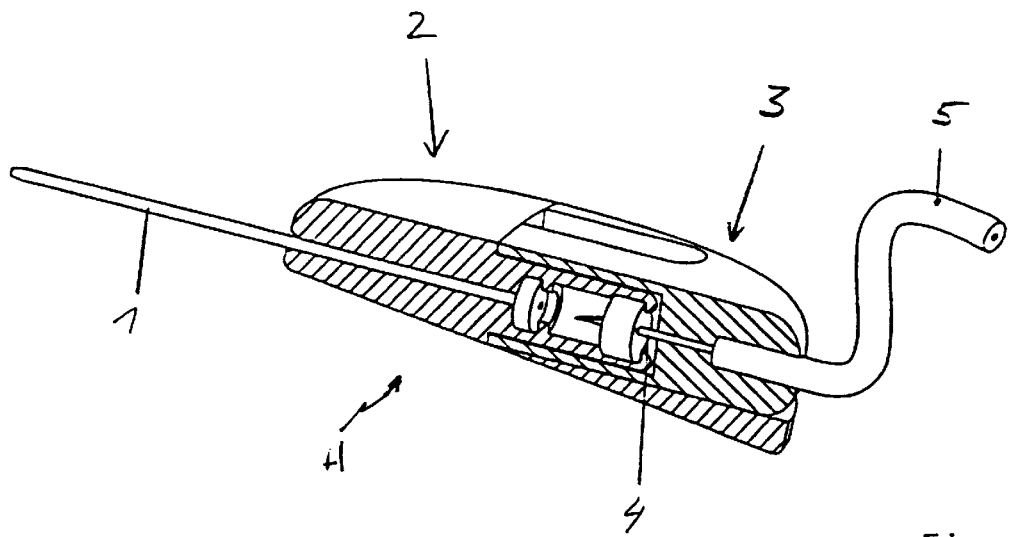
FIG. 5 depicts a second embodiment of a catheter head.
Figure 6:
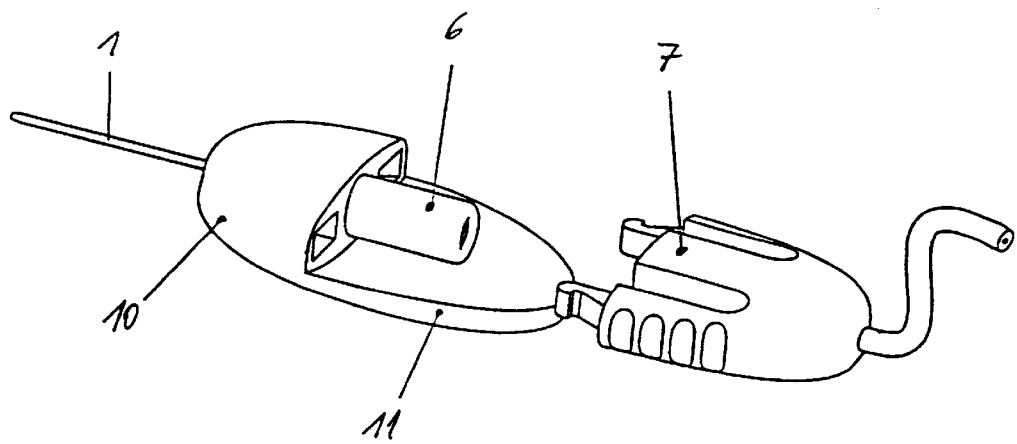
FIG. 6 is a longitudinal section of the catheter head shown in FIG. 5.

FIGS. 5 and 6 show a modified embodiment, in which the piercing needle is pierced through the same passage channel of the cannula housing 2 into which the connecting needle 4 is to be inserted after placing the cannula 1. With the exception of the arrangement of the piercing needle and the cannula 1, the catheter heads of FIGS. 5 and 6 correspond to the arrangement described above. Reference is therefore made to that description.

In embodiments according to the invention, the cannula housing 2 may be produced in a single injection moulding cycle. For this purpose, the prefabricated cannula 1 including its widened section 21 and possibly the septum 8 and the septum 22, are inserted into the injection moulding tool and directly moulded into the same as an integral part of the cannula housing 2. The required attachments in the shape of all-round shoulders surrounding the afore-mentioned components, are specified by the injection moulding tool. The septums 8 and 22 may also be inserted into the cannula housing 2, whereby the cannula housing 2 is remoulded in another production cycle for retaining the septums 8 and 22. Moulding the cannula 1 in particular is a considerable simplification of the process for manufacturing the cannula housing 2.

The foregoing description of the present invention has been presented for the purpose of illustration and description. They are not intended to be exhaustive or to limit the invention to the precise form disclosed. Modifications or variations are possible in light of the above teachings. The embodiments were chosen and described to provide an illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A catheter head for subcutaneous administration of a substance, comprising:
   a) a cannula housing carrying a cannula to be placed in tissue, and having a passage to said cannula for the substance, said cannula housing comprising an underside for flush positioning on a tissue surface,
   b) a needle holder including a feed line for conducting the substance and a connecting needle to be inserted into said passage of said cannula housing, wherein said needle holder and said cannula housing are coupled to each other, said needle holder forming a guide sleeve axially surrounding said connecting needle and being narrowly slide-guided over a cylindrical extension of said cannula housing, thereby sheathing both an inlet and a section of said passage of said cannula housing adjacent to said inlet, and
   c) guide means for positioning of said connecting needle and, during insertion of said connecting needle into said passage of said cannula housing, for guiding said needle holder at said cannula housing.

2. The catheter head as set forth in claim 1, wherein said guide sleeve comprises a closed jacket surface surrounding said connecting needle.

3. The catheter head as set forth in claim 1, wherein said cannula housing comprises a disc-shaped rear section and a thicker front section comprising said passage channel for receiving said cannula, and from which said cylindrical extension projects over said disc-shaped rear section.

4. The catheter head as set forth in claim 3, wherein a clearance remains between said cylindrical extension and an upper side of the said disc-shaped rear section for sliding over of the said guide sleeve.

5. The catheter head as set forth in claim 1, wherein an upper side of the cannula housing forms, during insertion of the connecting needle, a support and an additional slideway for said needle holder.

6. The catheter head as set forth in claim 1, wherein said upper side is adapted to an underside of said needle holder which is curved in cross direction to said connecting needle, said upper side thus forming said additional slideway, said additional slideway preferably extending parallel to said cylindrical extension.

7. The catheter head as set forth in claim 1, wherein an underside of said needle holder is mould positioned on an upper side of a rear section of said cannula housing during positioning and insertion of said connection needle.

8. The catheter head as set forth in claim 1, wherein said needle holder comprises an upper side symmetrical to its underside, wherein said underside and said upper side are preferably curving outwardly away from each other.

9. The catheter head as set forth in claim 1, wherein a piercing needle for said cannula projects through said cannula housing at an angle to the longitudinal direction of said inserted connecting needle, wherein said passage channel for said connecting needle leads at an angle into an additional passage for said piercing needle.

10. The catheter head as set forth in claim 1, wherein the prefabricated cannula is formed as an integral part of said cannula housing when injection-moulding said cannula housing.

11. A catheter head for subcutaneous administration of an active substance, comprising:
   a) a cannula housing comprising a cannula to be placed in tissue and a passage to said cannula being formed in said cannula housing, said cannula housing having an underside adapted for substantially flush positioning on a tissue surface and adapted for attachment to the tissue surface,
   b) a needle holder including a feed line for feeding the active substance and a connecting needle to be inserted into said passage of said cannula housing, wherein said needle holder and said cannula housing are connectable to each other, and
   c) guide means for positioning of said connecting needle and, during insertion of said connecting needle into said passage of said cannula housing, for guiding said needle holder at said cannula housing, wherein
   d) said needle holder forms a guide sleeve axially surrounding said connecting needle, said guide sleeve being narrowly slide-guided over a cylindrical extension of said cannula housing, sheathing both an inlet and a section of said passage of said cannula housing following said inlet.

* * * * *